United States Patent [19]

Samejima et al.

[11] 4,443,497

[45] Apr. 17, 1984

[54] METHOD OF PREPARING MICROCAPSULES

[75] Inventors: Masayoshi Samejima, Minoh; Goichi Hirata, Yawata, both of Japan

[73] Assignee: Tanabe Seiyaku Co., Ltd., Osaka, Japan

[21] Appl. No.: 333,026

[22] Filed: Dec. 21, 1981

[30] Foreign Application Priority Data

Jan. 19, 1981 [JP] Japan .................................. 56-6859

[51] Int. Cl.$^3$ .............................................. B01J 13/02
[52] U.S. Cl. ................................ 427/213.36; 424/19; 424/33; 424/35
[58] Field of Search ................. 252/316; 424/33, 19, 424/35; 427/213.36

[56] References Cited

U.S. PATENT DOCUMENTS

| | | | |
|---|---|---|---|
| 3,141,792 | 7/1964 | Lachman et al. | 424/31 X |
| 3,336,155 | 8/1967 | Rowe | 252/316 X |
| 3,405,070 | 10/1968 | Reyes | 252/316 |
| 3,943,063 | 3/1976 | Morishita et al. | 252/316 |
| 4,089,800 | 5/1978 | Temple | 252/316 |

FOREIGN PATENT DOCUMENTS 49-55820  5/1974  Japan .

OTHER PUBLICATIONS

Nakano et al.: "Sustained Urinary Excretion of Sulfamethizole...", International Journal of Pharmacology, 4, (1980), 291–298, Elsevier/North-Holland Biomedical Press.

*Primary Examiner*—Richard D. Lovering
*Attorney, Agent, or Firm*—Jordan B. Bierman; Linda Bierman

[57] ABSTRACT

Microcapsules are prepared by conducting the phase-separation of a coating polymer material in the presence of ethylcellulose. Ethylcellulose present in the phase separation system minimizes the coagulation of the coating polymer material.

10 Claims, No Drawings

METHOD OF PREPARING MICROCAPSULES

This invention relates to a method of preparing microcapsules. More particularly, it relates to preparation of a pharmaceutically active compound-containing microcapsules which are soluble in gastro-intestinal tracts.

It is known that microcapsules are prepared by taking advantage of the phase-separation of a coating polymer material in an organic solvent solution. For example, microcapsules containing sulfamethizole are prepared by coacervation of carboxymethyl ethylcellulose, an enteric coating polymer material, from an ethyl acetate solution thereof in the presence of polylactic acid (M.Nakano et al., International Journal of Pharmacology 4(1980), 291–298, Elsevier/North-Holland Biomedical Press). Moreover, potassium penicillin V is microencapsulated with coating polymer materials such as those soluble in stomach, intestines or both by adding an organic nonsolvent to a dispersion containing said coating polymer material and particles of said penicillin (core material) to induce liquid-liquid phase separation of the polymer on and around the particles of the core material (Fukushima et al., Japanese Patent Publication (unexamined) No. 55820/1974). However, for industrial production of microcapsules these known methods are still unsatisfactory in that it is difficult to recover the coated particles in discrete forms because of their adhesion and agglomeration. For example, when in said Nakano's method carboxymethyl ethylcellulose is used in an amount of not less than 0.1 gram per ml of the organic solvent, the liquid particles of the coating polymer material separated from the organic solvent solution are coagulated with the solid particles of the core material and it is almost impossible to recover free-flowing discrete microcapsules therefrom.

As an alternative to the above-mentioned methods, U.S. Pat. No. 3,336,155 discloses a method of making microcapsules by conducting the liquid-liquid phase separation of a coating polymer material such as styrene-maleic acid copolymer or polyvinylacetate in the presence of a mineral silicate. However, since in this method the large excess (e.g., about 2.5 to 5 grams per gram of the coating polymer material used) of the mineral silicate must be added intermittently during the microencapsulation step (i.e., the step of adding an organic nonsolvent to a dispersion containing the coating polymer and core materials), the mineral silicate is inevitably incorporated into the capsule walls of the microcapsules. Such mineral silicate incorporated into the capsule walls makes it difficult to obtain microcapsules of compact wall structure and also results in deterioration in the wall properties of the coating polymer material such as impermeability, flexibility, stability and so forth. Moreover, since the mineral silicate which remains in the dispersion without being incorporated into the capsule walls is separated as minute particles and are coated with the coating polymer materials, the microcapsules of an active ingredient used as the core material are contaminated with those of said silicate.

As a result of various investigations for making microcapsules by the use of an enteric coating polymer material or other coating polymer material soluble in gastrointestinal tracts, we have now found that the free-flowing microcapsules having uniform particle size can be obtained by effecting the phase separation-flocculation of said coating polymer material in the presence of ethylcellulose; and also that said ethylcellulose present in the phase separation system minimizes the coagulation of the coating polymer material or the adhesion or agglomeration of each microcapsules.

According to the present invention, microcapsules containing a pharmaceutically active compound which are soluble in gastro-intestinal tracts are prepared by the steps of:

(i) dissolving a coating polymer material (said polymer material being either a water-insoluble, acid-soluble coating polymer material, an enteric coating polymer material or an amphoteric coating polymer material) and ethylcellulose in a solvent, (ii) dispersing particles of a pharmaceutically active compound (core material) to the solution, (iii) adding to the dispersion an organic liquid which is miscible to the solvent and which is nonsolvent for said coating polymer material and the core material, thereby forming coating walls of said coating polymer material on and around the particles of the core material, and then (iv) recovering the thus-formed microcapsules therefrom.

A wide variety of coating polymer materials can be used as the wall-forming material of the present invention. One of representative examples of said coating polymer material is an enteric coating polymer material, i.e., a coating polymer material soluble in water at a pH of not lower than 5. Preferred examples of such enteric coating polymer material include carboxyalkyl.alkylcellulose (e.g., carboxymethyl.ethylcellulose); organic dicarboxylic acid esters such as phthalic acid ester and succinic acid ester of alkylcellulose, hydroxyalkyl.alkylcellulose or cellulose.acetate (e.g., methylcellulose phthalate, hydroxypropyl.methylcellulose phthalate, hydroxyethyl ethylcellulose phthalate, cellulose acetate succinate, cellulose acetate phthalate); copolymers of an alkenylcarboxylic acid and an alkyl ester of said alkenylcarboxylic acid (e.g., methacrylic acid.methyl methacrylate copolymer, methacrylic acid.methyl acrylate copolymer, methacrylic acid.ethyl acrylate copolymer); and copolymers of an alkenylcarboxylic acid and two alkyl esters of said alkenylcarboxylic acid (e.g., methacrylic acid.methyl acrylate.methyl methacrylate copolymer, methacrylic acid.methyl methacrylate.octyl acrylate copolymer). Another example of the wall-forming material which can be used in the present invention is a water-insoluble, acid-soluble coating polymer material (i.e., a coating polymer material soluble in water at a pH of not higher than 5), and preferred examples of such coating polymer material include copolymers of (A) dialkylaminoalkyl ester of alkenylcarboxylic acid and (B) one or two alkyl esters of alkenylcarboxylic acid (e.g., dimethylaminoethyl methacrylate.methyl methacrylate copolymer, dimethylaminoethyl methacrylate.methyl methacrylate.butyl methacrylate copolymer); and polyvinylacetal dialkylaminoacetate e.g., polyvinylacetal diethylaminoacetate). A further example of the wall material of the present invention is an amphoteric coating polymer material, i.e., a coating polymer material soluble in water at a pH of not lower than 6 or a pH of not higher than 4.5. Preferred examples of such amphoteric coating polymer material include copolymers of (A) vinylpyridine or alkylvinylpyridine, (B) alkenylcarboxylic acid and (C) a monomer selected from acrylonitrile, styrene and an alkyl ester of alkenylcarboxylic acid (e.g., 2-vinylpyridine.methacrylic acid.methyl acrylate copolymer, 2-methyl-5-vinylpyridine.methacrylic acid.methyl acrylate copolymer, 2-vinyl-5-ethylpyridine.methacrylic acid.styrene copolymer, 2-vinylpyridine.methacrylic acid.acrylonitrile copolymer, 2-vinyl-5-ethylpyridine.methacrylic acid.-methyl acrylate copolymer). Further examples of the coating polymer material which may be used in the present invention include enteric coating polymer materials such as starch acetate phthalate, polyvinylalcohol phthalate, polyvinylbutylate phthalate, polyvinylacetoacetal phthalate, vinylacetate.maleic acid anhydride copolymer, vinylbutylether.maleic acid anhydride copolymer, styrene.maleic acid monoester copolymer, styrene.maleic acid anhydride.maleic acid monolauryl ester copolymer and styrene.acrylic acid copolymer; water-insoluble, acid-soluble coating polymer materials such as benzylaminomethylcellulose, diethylaminomethylcellulose, pyperidyl.ethyl.hydroxyethylcellulose, cellulose acetate diethylaminoacetate, cellulose acetate.dibutylamino.hydroxypropylether, vinyldiethylamine.vinylacetate copolymer, vinylbenzylamine.vinylacetate copolymer, vinylpiperidylacetoacetal, vinylacetate copolymer, polyvinylacetal.diethylaminoacetate, polydimethylaminoethyl-methacrylate and poly-diethylaminomethylstyrene; and amphoteric coating polymer materials such as carboxymethyl.piperidyl.starch, carboxymethyl(benzylamino)cellulose, poly-2-(vinylphenyl)glycine and N-vinylglycine.styrene copolymer. In making the microcapsules of the present invention it is preferred that these coating polymer materials are used in an amount of about 0.02 to about 10 grams, especially about 0.1 to about 5 grams, per gram of the core material used.

In making microcapsules by the use of the abovementioned coating polymer materials, ethylcellulose having an ethoxy content of about 44 to about 55 w/w % is successfully used to prevent the coagulation of the coating polymer materials and adhesion or agglomeration of each microcapsules. It is preferred that the viscosity of said ethylcellulose when measured at 25° C. with respect to a 5 w/w % solution of it in toluene-ethanol (3:1 or 4:1) is within the range of about 3 to about 500 cP, especially about 40 to about 350 cP. It is also preferred that said ethylcellulose is used in an amount of about 0.05 to about 5 grams, especially about 0.1 to 2 grams, per gram of the coating polymer material used.

Any one of pharmaceutically active compounds (or medicaments) can be used as the core material to be microencapsulated in the present invention. Such pharmaceutically active compound or medicament to be microencapsulated may be either solid, gel or semi-solid. In order to prepare a homogeneous dispersion at the microencapsulation step, it is preferred that said pharmaceutically active compound or medicament has a particle size of about 5 to about 1000μ, especially 50 to 500μ. Eligible for microencapsulation as solids are particles of material such as, for example, vitamines (e.g., ascorbic acid), amino acids (e.g., potassium aspartate, magnesium aspartate), minerals (e.g., potassium chloride), anti-microbial agents (e.g., benzylpenicillin potassium salt, sulfomethizole), anti-tumor agents (e.g., 5-fluorouracil, bleomycin hydrochloride), metabolic agents (e.g., glutathion), cardiovascular agents (e.g., diltiazem hydrochloride), analgesics (e.g., acetylsalicylic acid), anti-histaminics (e.g., diphenhydramine hydrochloride), neuro-psycotropic agents (e.g., calcium N-($\gamma$,$\gamma$-dihydroxy-$\beta$,$\beta$-dimethylbutyryl)-$\gamma$-aminobutyrate), agents affecting digestive organs (e.g., methylmethionine sulfonium chloride, di-(2-thienyl)-(N-methyl-5-methoxy-3-piperidilidene)methane methylbromide, precipitated calcium carbonate, 2-dimethylamino-2-phenylbutyl 3,4,5-trimethoxybenzoate hydrogen maleate), agents affecting respiratory organs (e.g., trimethoquinol hydrochloride), and so forth. Also eligible for microencapsulation as semi-solids are, for example, slurrys such as a slurry composed of 30 w/w % of sodium polyacrylate, 40 w/w % of water and 30 w/w % of 5-fluorouracil. And pharmaceutically active compounds in the form of "gel" which can be microencapsulated include, for example, dextran gel having a medicament (e.g., methylmehionine sufonium chloride) adsorbed therein, formalin-treated gelatin gel having dispersed a medicament (e.g., sulfamethomidine) therein, and so forth.

Moreover, any solvents which dissolve the coating polymer material and ethylcellulose and which do not dissolve the core material can be used as the solvent of the invention. Examples of such solvent are chlorinated hydrocarbons of one to three carbon atoms (e.g., chloroform, tetrachloromethane, methylenedichloride, ethylenedichloride), alkanols of one to four carbon atoms (e.g., methanol, ethanol, isopropanol), a mixture of said alkanol and water, alkanones of three to five carbon atoms (e.g., acetone, methylethylketone), a mixture of said alkanol and alkanone, ethyl acetate, a mixture of said alkanol and ethyl acetate, 2-methoxyethanol, 2-ethoxyethanol, 2-butoxyethanol, diethyleneglycol, dioxane, dimethyl formamide, epichlorohydrine, trimethyl phosphate, triethyl phosphate, tetrahydrofuran, diacetone alcohol and the like.

In making the microcapsules of a pharmaceutically active compound according to the present invention, it is preferable to dissolve the coating polymer material and ethylcellulose in a solvent such as those mentioned above, and then dispersing the particles of a pharmaceutically active compound (core material) to the solution under stirring. It is also preferable to use the coating polymer material and ethylcellulose so that the concentration of the coating polymer material in the solution becomes about 0.1 to about 40 w/w %, especially about 2 to about 20 w/w %, and the concentration of ethylcellulose in the solution becomes about 0.1 to about 20 w/w %, especially about 0.2 to 10 w/w %. Then, a nonsolvent is added gradually to the dispersion of the core material to cause liquid-liquid phase separation of the coating polymer material. The temperature is not critical in the invention, and the above-mentioned operations may be carried out at any temperature up to the boiling point of the solvent, nonsolvent or a mixture thereof to be used.

In the present invention, the term "nonsolvent" means an organic liquid which is miscible to the solvent and which is nonsolvent for the coating polymer material and the core material. Suitable examples of such nonsolvent include hydrocarbons (e.g., n-heptane, n-hexane, cyclohexane, cyclohexene, petroleum ether), ethers (e.g., ethyl ether, isopropyl ether), and the like. Moreover, acetone may be used as the nonsolvent depending on the coating polymer material to be used. The amount of the nonsolvent to be used may vary over a wide range depending on the solvent and coating polymer material, but it is generally preferable to use nonsolvent in an amount of one to 6 ml per ml of the solvent.

By adding the nonsolvent gradually to the dispersion of the core material the coating polymer material separates out from the dispersion to form a liquid phase or gel depositing on and around the particles of the core material, and said coating polymer material thus deposited forms seamless and complete walls on further addition of the nonsolvent. In carrying out this microencapsulation step ethylcellulose can successfully prevent the agglomeration of each microcapsules because, during said step, each embryonic capsules formed are protected with the adsorption layer of ethylcellulose formed on the surface of said capsules.

Further, in the method of the present invention, a plasticizer may be used in combination with ethylcellulose. Suitable examples of said plasticizer which may be used in the present invention include $C_{10-18}$ alkanoic acid esters of glycerin or acetylglycerin such as glycerin monocaprylate, glycerin monolaurate, glycerin monooleate, acetylglycerin monostearate; organopolysiloxanes such as dimethylpolysiloxane, methylphenylpolysiloxane and silicon.glycol copolymer; propyleneglycol; polyethyleneglycol; glycerin monoacetate, glycerin diacetate, glycerin triacetate, polyvinylacetate, polylactic acid; and the like. It is preferable to use such plasticizer in an amount of about 0.01 to 1.0 gram per gram of the coating polymer material. It is also preferable that said plasticizer is added to the dispersion of the core material prior to addition of the nonsolvent, and that the concentration of the plasticizer in the dispersion is about 0.1 to 30 w/v %.

The microcapsules thus obtained may be recovered by conventional manners such as, for example, decantation, centrifugation, filtration and so forth. In addition, the microcapsules containing a pharmaceutically active compound can be readily obtained substantially free of ethycellulose by washing the thus-obtained microcapsules with a mixture of the nonsolvent and an organic solvent which dissolves ethylcellulose but does not dissolve the core material and the coating polymer material. If required, the microcapsules of the invention may be further washed with the nonsolvent.

According to the above-mentioned method of the present invention, the microcapsules of uniform particle size which as such can be used as granules or powder are obtained in a high yield because ethylcellulose is adsorbed on the surface of the embryonic capsules (which are formed by flocculation of the coating polymer material on the surface of the core material) before the deposited coating polymer material becomes solid, and, therefore, can efficiently prevent each microcapsule from agglomerating together into large lumps each containing a myriad of individual capsules. In addition, the microcapsules free from said ethylcellulose can be readily obtained by washing them as mentioned above to remove ethylcellulose adsorbed on the capsules. Moreover, the method of the present invention can be conducted without inflammable and/or explosive conditions of the solvent because the microencapsulation thereof proceeds smoothly at below room temperature or, if required, at a temperature below 0° C. Further, when ethylcellulose is used in combination with a plasticizer, said plasticizer serves to increase the viscoelasticity or flexibility of the coating polymer material because of incorporation of a small amount of the plasticizer into the coating walls of the capsules. Such increased viscoelasticity serves to improve the wall characteristics of the coating polymer material deposited on the core material, i.e., to form the free-flowing, discrete microcapsules of compact and complete wall structure.

Practical and presently-preferred embodiments of the present invention are illustratively shown in the following lines. Throughout the specification and claims, the term "alkyl" should be interpreted as referring to alkyl of one to 8 carbon atoms, especially that of one to four carbon atoms. On the other hand, the term "alkenyl" should be interpreted as referring to alkenyl of 3 to 5 carbon atoms, especially that of 3 to 4 carbon atoms.

Experiment I

Microcapsules containing trimethoquinol hydrochloride (chemical name: 1-1-(3,4,5-trimethoxybenzyl)-6,7-dihydroxy-1,2,3,4-tetrahydroisoquinoline hydrochloride monohydrate) were prepared according to the following methods. Then, the yield of microcapsules thus obtained, the amount of the active ingredient contained in the microcapsules, the release rate (%) of the active ingredient therefrom in a simulated gastric fluid and the 100% release time (i.e., a period of time which was necessary to release 100% of the active ingredient from the microcapsules) in a buffer solution (pH 6.8) were examined, respectively.

(i) Core material:

Trimethoquinol hydrochloride having a particle size of 350–420μ was used as the core material.

(ii) Preparation of microcapsules:

180 g of hydroxypropyl methylcellulose phthalate (methoxy content: 20 w/w %, hydroxypropyl content: 7 w/w %, carboxybenzoyl content: 31 w/w %; said cellulose phthalate derivative being soluble in water at a pH not lower than 5.5) and an amount of ethylcellulose and a plasticizer shown in the following Table 1 were dissolved in 2 liters of acetone. After 300 g of trimethoquinol hydrochloride were dispersed in the solution, 4 liters of cyclohexane were added gradually to the dispersion for about 120 minutes under stirring at 400 r.p.m.. The microcapsules thus formed were recovered by filtration, washed and dried. Said microcapsules were passed through JIS (Japanese Industrial Standard) standard sieve (500μ aperture) and then JIS standard sieve (105μ aperture). The microcapsules which passed through the former sieve but did not pass through the latter sieve were collected, whereby trimethoquinol hydrochloride- 0 containing microcapsules which met the requirements of "Fine Granules" specified in THE PHARMACOPOEIA OF JAPAN 9th-Edition were obtained.

TABLE 1

| Experiment Nos. | Amount of ethylcellulose[1] (viscosity) | Plasticizer and amount thereof use | Solvent used for washing microcapsules | Yield of microcapsules[2] |
|---|---|---|---|---|
| 1 | 120 g (100 cP) | glycerin triacetate 70 g | acetone-cyclohexane (1:2), and cyclohexane | 473 g |
| 2 | 120 g (100 cP) | Propylene glycol 35 g | same as above | 461 g |
| 3 | 120 g (100 cP) | Polyvinyl-acetate 60 g | chloroform-cyclohexane (1:2), and cyclohexane | 469 g |
| 4 | 120 g (100 cP) | — | acetone-cyclohexane (1:2), and cyclohexane | 464 g |
| (Control) 5 | — | — | | discrete microcapsules could not be obtained because of agglomeration |

TABLE 1-continued

| Experiment Nos. | Amount of ethylcellulose[1] (viscosity) | Plasticizer and amount thereof use | Solvent used for washing microcapsules | Yield of microcapsules[2] of each capsule |
|---|---|---|---|---|

Note:
[1]Ethylcellulose haveing ethoxy content of 48.5 w/w % was used. The viscosity was examined at 25° C. with respect to a toluene-ethanol (4:1) solution containing 5 w/w % of said ethylcellulose.
[2]Amount of the microcapsules which met the requirements of "Fine Granules" specified in THE PHARMACOPOEIA OF JAPAN 9th-Edition (iii) Effect of capsule wall on the release of active ingredient from microcapsules:

The microcapsules obtained in paragraph (ii) were added to a simulated gastric fluid specified in THE PHARMACOPOEIA OF JAPAN 9th-Edition, and the mixture was stirred at 37° C. for 3 hours. After the experiment, the release rate of trimethoquinol hydrochloride (active ingredient) in the simulated fluid was estimated based on the amount of said active ingredient released from the microcapsules.

On the other hand, the 100% release time of the active ingredient from the microcapsules was examined by adding said microcapsules to a standard solution of pH 6.8 specified in the British Pharmacopoeia (1973) and then measuring the time required to release 100% of the active ingredient from the microcapsules.

As can be seen in the following Table 2, in the method of the present invention the microcapsules could be obtained in a high yield. Moreover, the microcapsules thus obtained had excellent properties as enteric coated microcapsules because they showed slow release of the active ingredient in the simulated gastric fluid, but rapid release thereof at pH 6.8.

TABLE 2

| Experiment Nos. | Amount of trimethoquinol hydrochloride contained in microcapsules. (%) | Yield of microcapsules[1] (%) | Amount of active ingredient released in simulated gastric fluid (%) | 100% release time (minutes) |
|---|---|---|---|---|
| (The methods of the present invention) | | | | |
| 1 | 62.5 | 98.6 | 4.2 | 38 |
| 2 | 63.7 | 97.8 | 10.8 | 24 |
| 3 | 62.6 | 97.9 | 2.1 | 46 |
| 4 | 63.9 | 98.9 | 8.4 | 40 |
| (Control) | | | | |
| 5[2] | 62.5 | 0 | 100 | <27 |

Note:
[1]The yield of microcapsules was calculated according to the following formula:
$$Y = \frac{a}{b} \times Y_{obs}$$
a: amount (%) of active ingredient contained in microcapsules
b: amount (grams) of active ingredient used
Yobs: yield (grams) of microcapsules which met the requirements of "Fine Granules" specified in THE PHARMACOPOEIA OF JAPAN 9th-Edition.
[2]Since microcapsules which met the requirements of "Fine Granules" specified as above could not be obtained in the control group, the agglomerated microcapsules were used as such for the experiments.

Experiment II

Glutathion-containing microcapsules were prepared according to the following methods. Then, the yield of microcapsules was obtained, the amount of the active ingredient contained in the microcapsules, the 100% release time (i.e., a period of time which was necessary to release 100% of the active ingredient from the microcapsules) in a simulated gastric fluid and the 50% release time of said microcapsules in a buffer solution (pH 6.0) were examined, respectively.

(i) Core material:

20 parts (by weight) of an aqueous 15 w/v % methylcellulose solution were added to a mixture of 40 parts (by weight) of glutathion and 57 parts (by weight) of lactose, and the mixture was granulated and dried in a conventional manner. The granules (particle size: 350–420μ) thus obtained were used as the core material.

(ii) Preparation of microcapsules:

180 g of 2-methyl-5-vinylpyridine.methyl acrylate.methacrylic acid copolymer (molar ratio=2.4:1.9:1) (this copolymer being soluble in water at a pH lower than 4 or higher than 7 but not soluble in water at a pH of 4–7) and 100 g of ethylcellulose (ethoxy content: 48–50 w/w %) were dissolved in 2 liters of methanol, and 300 g of the glutathion-containing granules were dispersed therein. 2 liters of acetone and 8 liters of n-hexane were added gradually to the dispersion. The microcapsules thus formed were recovered by filtration, and washed with acetone-n-hexane (1:2) and n-hexane, successively. After said microcapsules were dried, microcapsules which passed through JIS standard sieve (500μ aperture) but did not pass through JIS standard sieve (105μ aperture) were collected. 467 g of glutathion-containing microcapsules which met the requirements of "Fine Granules" specified in THE PHARMACOPOEIA OF JAPAN 9th-Edition were thereby obtained.

On the other hand, when glutathion-containing microcapsules (control group) were prepared in the same manner as above without using ethylcellulose, the microcapsules were agglomerated together into large lumps each containing a myriad of individual capsules and no microcapsules satisfying the above-mentioned requirements of "Fine Granules" could be obtained.

(iii) Estimation of release time:

The microcapsules obtained in paragraph (ii) were added to a simulated gastric fluid specified in THE PHARMACOPOEIA OF JAPAN 9th-Edition, and the mixture was stirred at 37° C. The amount of the active ingredient released from the microcapsules was examined with the lapse of time, and the 100% release time of the active ingredient from the microcapsules was estimated therefrom.

On the other hand, the 50% release time of the active ingredient from the microcapsules was examined by adding said microcapsules to a standard solution of pH 6.0 specified in the British Pharmacopoeia (1973) and then measuring the time required to release 50% of the active ingredient from the microcapsules.

It can be seen from the following Table 3 that the glutathion-containing microcapsules could be obtained in a high yield according to the present invention. Moreover, the microcapsules thus obtained by the use of 2-methyl-5-vinylpyridine.methyl acrylate.methacrylic acid copolymer (said polymer being soluble in both stomach and intestines) as the wall-forming material were quite stable in a buffer solution of pH 6.0. This suggests that, when administered orally, said microcapsules show no substantial release of the active ingredient in the oral cavity.

TABLE 3

| Experiment Nos. | Viscosity of ethylcellulose[1] | Yield of microcapsules[2] (%) | Amount of glutathion contained in microcapsules (%) | 100% release time[3] (minutes) | 50% release time[4] (minutes) | Taste[5] |
|---|---|---|---|---|---|---|
| (The methods of the present invention) | | | | | | |
| 1 | 10 cP | 96.1 | 26.9 | ≦2 | 40 | (−) |
| 2 | 20 cP | 95.0 | 26.7 | ≦2 | 58 | (−) |
| 3 | 45 cP | 96.9 | 25.2 | ≦5 | 75 | (−) |
| 4 | 100 cP | 97.3 | 25.0 | ≦5 | 70 | (−) |
| (Control) | | | | | | |
| 5[6] | — | 0 | 25.1 | ≦2 | 15 | (+) |

Note:
[1] The viscosity of ethylcellulose was examined in the same manner as described in the footnote of Table 1.
[2] The yield of microcapsules was calculated in the same manner as described in the footnote of Table 2.
[3] A period of time which was necessary to release 100% of the active ingredient in the simulated gastric fluid.
[4] A period of time which was necessary to release 50% of the active ingredient in the buffer solution of pH 6.0.
[5] (−): tasteless
(+): bitter taste
[6] Since microcapsules which met the requirements of "Fine Granules" specified as above could not be obtained in the control group, the agglomerated microcapsules were used as such for the experiments.

Example 1

180 g of methyl acrylate.methacrylic acid.methyl methacylate copolymer (molar ratio=1:1.2:1.2), 180 g of acetyl glycerin monostearate and 120 g of ethylcellulose [ethoxy content: 48.5%, viscosity (measured at 25° C. with respect to a toluene-ethanol (4:1) solution containing 5 w/w % of said ethylcellulose): 45 cP] were dissolved in 2 liters of ethanol. 300 g of glutathion having a particle size of 350–420μ were dispersed in the solution, and 4 liters of cyclohexane were added gradually to the dispersion under stirring at 400 r.p.m.. The microcapsules thus obtained were recovered by filtration, washed with ethanolcyclohexane (1:3) and cyclohexane, and then dried. Then, said microcapsules were passed through JIS standard sieve (500μ aperture), whereby 464 g of glutathion-containing microcapsules which met the requirements of "Fine Granules" specified in THE PHARMACOPOEIA OF JAPAN 9th-Edition were obtained.

Amount of glutathion contained in the microcapsules: 62.7 w/w %
Amount of glutathion released in a simulated gastric fluid (estimated in the same manner as described in Experiment I, paragraph (iii)): 15%
100% release time of glutathion in a standard solution of pH 6.8 (estimated in the same manner as described in Experiment I, paragraph (iii)):≦28 minutes.

Example 2

Microcapsules were prepared in the same manner as described in Example 1 except that 180 g of cellulose acetate phthalate (acetyl content: 21.8 w/w %, carboxybenzoyl content: 32.5 w/w %) and 35 g of polyethyleneglycol 1500 were used instead of methyl.acrylate methacrylic acid.methyl methacrylate copolymer and acetyl glycerin monostearate. 461 g of glutathion-containing microcapsules which met the requirements of "Fine Granules" specified above were obtained.

Amount of glutathion contained in the microcapsules: 63.0 w/w %
Amount of glutathion released in a simulated gastric fluid (estimated in the same manner as described in Experiment I, paragraph (iii)): 17%
100% release time of glutathion in a standard solution of pH 6.8 (estimated in the same manner as described in Experiment I, paragraph (iii)): ≦34 minutes.

Example 3

180 g of 2-vinylpyridine.methyl acrylate.methacrylic acid copolymer (molar ratio=1:2:1), 120 g of ethylcellulose (the ethoxy content and viscosity thereof are the same as defined in Example 1) and 144 g of glycerin monocaprylate were dissolved in 2 liters of methanol. 300 g of alloprinol (chemical name: 1H-pyrazolo[3,4-d]pyrimidine-4-ol) having a particle size of 74–177μ were dispersed in the solution. 2 liters of acetone and then 8 liters of n-hexane were added dropwise to the dispersion under stirring at 400 r.p.m.. The microcapsules thus obtained were recovered by filtration, washed with acetone-n-hexane (1:2) and n-hexane, and then dried. Then, said microcapsules were passed through JIS standard sieve (350 aperture), whereby 469 g of alloprinol-containing microcapsules which met the requirements of "Pulvers" specified in THE PHARMACOPOEIA OF JAPAN 9th-Edition were obtained.

Amount of alloprinol contained in the microcapsules: 62.7 w/w %
100% release time of alloprinol in a simulated gastric fluid (estimated in the same manner as described in Experiment II, paragraph (iii)): ≦5 minutes.
50% release time of alloprinol in a standard solution of pH 6.0 (estimated in the same manner as described in Experiment II, paragraph (iii)): 90 minutes.

Example 4

180 g of polyvinylacetal diethylaminoacetate (nitrogen content: 2.0 w/w %), 100 g of ethylcellulose (the ethoxy content and viscosity thereof are the same as defined in Example 1) and 70 g of glycerin triacetate were dissolved in 2 liters of acetone. 300 g of a mixture of potassium aspartate and magnesium aspartate (quantitative ratio =1:1, particle size: 105–350μ) were dispersed in the solution, and 35 liters of ethylether were added gradually to the dispersion at −20° C. under stirring at 300 r.p.m.. The microcapsules thus obtained were recovered by filtration, washed with acetone-ethylether (1:3) and ethylether, and then dried. Then, said microcapsules were passed through JIS standard sieve (500μ aperture), whereby 471 g of aspartate-containing microcapsules which met the requirements of "Fine Granules" specified above were obtained.

Amount of potassium aspartate contained in the microcapsules: 31.5%
Amount of magnesium aspartate contained in the microcapsules: 31.7%
100% release time of potassium aspartate in a simulated gastric fluid (estimated in the same manner as described in Experiment II, paragraph (iii)):≦4 minutes.

Example 5

180 g of hydroxypropyl methylcellulose phthalate (methoxy content: 22 w/w %, hydroxypropyl content: 8 w/w %, carboxybenzoyl content: 24 w/w %), 120 g of ethylcellulose [ethoxy content: 48.5 w/w %, viscosity (measured at 25° C. with respect to a toluene-ethanol (4:1) solution containing 5 w/w % of said ethylcellulose): 100 cP] and 100 g of dimethylpolysiloxane (viscosity measured at 25° C.:200 cP) were dissolved in a mixture of 750 ml of acetone, 750 ml of methanol and 900 ml of cyclohexane. 300 g of potassium chloride (core material) having a particle size of 149–250μ were dispersed in the solution, and 3 liters of cyclohexane were added gradually at 5° C. under stirring at 300 r.p.m.. The microcapsules thus obtained were recovered by filtration, washed at 5° C. with methanol-acetone-cyclohexane (1:1:5) and n-hexane, and then dried. Then, said microcapsules were passed through JIS standard sieve (350μ aperture), whereby 472 g of potassium chloride-containing microcapsules which met the requirements of "Pulvers" specified above were obtained.

Amount of potassium chloride contained in the microcapsules: 62.6 w/w %
  Amount of potassium chloride released in a simulated gastric fluid (estimated in the same manner as descrbied in Experiment I, paragraph (iii)): 20%
  100% release time of potassium chloride in a standard solution of pH 6.8 (estimated in the same manner as described in Experiment I, paragraph (iii)): ≦17 minutes

Example 6

200 g of carboxymethyl ethylcellulose (degree of substitution of ethoxy group/mol of glucose=0.65), 110 g of ethylcellulose (the ethoxy content and viscosity thereof are the same as defined in Example 1) and 40 g of polylactic acid were dissolved in 2 liters of ethylacetate. 300 g of sulfamethizole having a particle size of 210–297μ were dispersed in the solution. After cooling the dispersion to −10° C., 5 liters of ethylether were added gradually thereto at the same temperature under stirring at 350 r.p.m.. The microcapsules thus obtained were recovered by filtration, washed at −10° C. with ethylacetate-ethylether (1:2.5) and n-hexane, and then dried. Then, said microcapsules were passed through JIS standard sieve (350μ aperture), whereby 520 g of sulfamethizole-containing microcapsules which met the requirements of "Pulvers" specified above were obtained.

Amount of sulfamethizole contained in the microcapsules: 56.1 w/w %
  Amount of sulfamethizole released in a simulated gasric fluid (estimated in the same manner as described in Experiment I, paragraph (iii)): 2.1%
  100% release time of sulfamethizole in a standard solution of pH 6.8 (estimated in the same manner as described in Experiment I, paragraph (iii)): ≦21 minutes. Example 7

Microcapsules were prepared in the same manner as described in Example 1 except that 180 g of methyl acrylate. methacrylic acid copolymer (molar ratio=1:1) and 30 g of polylactic acid were used instead of methyl acrylate.methacrylic acid.methyl methacrylate copolymer and acetyl glycerin monostearate. 480 g of glutathion-containing microcapsules which met the requirements of "Fine Granules" specified above were obtained.

Amount of glutathion released in a simulated gastric fluid (estimated in the same manner as described in Experiment I, paragraph (iii)): 11%
  100% release time of glutathion in a standard solution of pH 6.8 (estimated in the same manner as described in Experiment I, paragraph (iii)): ≦23 minutes.

Example 8

240 g of dimethylaminoethyl methacrylate.methyl methacrylate copolymer (molar ratio=1:1) and 140 g of ethylcellulose [ethoxy content: 54.8 w/w %, viscosity (measured at 25° C. with respect to a toluene-ethanol (4:1) solution containing 5 w/w % of said ethylcellulose): 5 cP] were dissolved in 2 liters of acetone-cyclohexane (1:3.8) 300 g of diltiazem hydrochloride having a particle size of 210–297μ were dispersed in the solution, and 40 liters of cyclohexane were added gradually to the dispersion at 40° C. under stirring at 300 r.p.m.. The microcapsules thus obtained were recovered by filtration, washed at 40° C. with cyclohexane and at 6° C. with n-hexane, and then dried. Then, said microcapsules were passed through JIS standard sieve (350μ aperture), whereby 534 g of diltiazem hydrochloride-containing microcapsules which met the requirements of "Pulvers" specified above were obtained.

Amount of diltiazem hydrochloride contained in the microcapsules: 55.6 w/w %
  100% release time of diltiazem hydrochloride in a simulated gastic fluid (estimated in the same manner as discribed in Experiment II, paragraph (iii)): ≦10 minutes.
  50% release time of diltiazem hydrochloride standard solution of pH 6.0 (estimated in the same manner as described in Experiment II, paragraph (iii)): 70 minutes.

Example 9

Microcapsules were prepared in the same manner as described in Example 1 except that 180 g of methacrylic acid.methyl methacrylate copolymer (molar ratio=1:1) and 20 g of glycerin monoacetate were used instead of methyl acrylate.methacrylic acid.methyl methacrylate copolymer and acetyl glycerin monostearate. 466 g of glutathion-containing microcapsules which met the requirements of "Fine Granules" specified above were obtained.

Example 10

Microcapsules were prepared in the same manner as described in Example 1 except that 180 g of methacrylic acid. methyl methacrylate copolymer (molar ratio=1:2) and 20 g of glycerin monoacetate were used instead of methyl acrylate.methacrylic acid.methyl methacrylate copolymer and acetyl glycerin monostearate. 470 g of gluththion-containing microcapsules which met the requirements of "Fine Granules" specified above were obtained.

Example 11

Microcapsules were prepared in the same manner as described in Example 1 except that 180 g of methacrylic acid.ethyl acrylate copolymer (molar ratio=1:1) and 20 g of glycerin diacetate were used instead of methyl acrylate.methacrylic acid.methyl methacrylate copolymer and acetyl glycerin monostearate. 461 g of glutathion-containing microcapsules which met the requirements of "Fine Granules" specified above were obtained.

Example 12

200 g of 2-dimethylaminoethyl methacrylate.methyl methacrylate.butyl methacrylate copolymer (molar ratio=2:3:1) and 100 g of ethylcellulose [ethoxy content: 48.1%, viscosity (measured at 25° C. with respect to a toluene-ethanol (4:1) solution containing 5 w/w % of said ethylcellulose): 200 cP] were dissolved in 2 liters of acetone-isopropanol (1:1). 300 g of glutathion having a particle size of 149–297μ were dispersed in the solution, and 8 liters of n-hexane were added gradually to the dispersion at 5° C. under stirring at 400 r.p.m.. The microcapsules thus obtained were recovered by filtration, washed with n-hexane and dried. Then, said microcapsules were passed through JIS standard sieve (350μ aperture), whereby 490 g of glutathion-containing microcapsules which met the requirements of "Pulvers" specified above were obtained.

We claim:

1. A method of preparing microcapsules which comprises:
   (i) dissolving a coating polymer material which is selected from the group consisting of (a) water-insoluble, acid-soluble coating polymer material, (b) enteric coating polymer material and (c) amphoteric coating polymer material; and 0.05 to 5 grams of ethylcellulose having an ethoxy content of 44–55 w/w % per gram of said coating polymer material; in a solvent selected from the class consisting of a chlorinated hydrocarbon having one to three carbon atoms, an alkanol having one to four carbon atoms, an alkanone having three to five carbon atoms, a mixture of said alkanol and said alkanone, 2-methoxyethanol, 2-ethoxyethanol, 2-butoxyethanol, dioxane, epihalohydrin, trimethyl phosphate, triethyl phosphate, tetrahydrofuran and diacetone alcohol to form a solution;
   (ii) dispersing particles of a pharmaceutically active compound as a core material in said solution to form a dispersion;
   (iii) adding an organic liquid which is miscible with said solvent and which is a nonsolvent for said coating polymer material and the pharmaceutically active compound to said dispersion thereby forming coating walls of said coating polymer material on and around said particles of said core material, whereby the ethyl cellulose present minimizes the coagulation of the coating polymer material and/or the adhesion or agglomeration of the thus-formed microcapsules, and then
   (iv) recovering the thus-formed microcapsules therefrom.

2. The method according to claim 1, wherein said coating polymer material is selected from the class consisting of carboxyalkyl alkylcellulose; phthalic or succinic acid ester of alkyl cellulose, hydroxyalkyl alkylcellulose, cellulose acetate; copolymers of acrylic or methacrylic acid and alkyl esters of acrylic or methacrylic acid; copolymers of acrylic or methacrylic acid, alkyl acrylate and alkyl methacrylate; copolymers of (A) dialkylaminoalkyl methacrylate and (B) an alkyl methacrylate; copolymers of (A) dialkylaminoalkyl methacrylate, (B) a first alkyl methacrylate, and (C) a second alkyl methacrylate; polyvinylacetal dialkylaminoacetate; and copolymers of (A) vinylpyridine or alkylvinylpyridine, (B) acrylic or methacrylic acid, and (C) a monomer selected from acrylonitrile, styrene and alkyl ester of acrylic or methacrylic acid.

3. The method according to claim 1, wherein said coating polymer material is selected from carboxyalkyl alkylcellulose; phthalic acid ester of hydroxyalkyl alkylcellulose or cellulose acetate; copolymers of methacrylic acid and alkyl acrylate; copolymers of methacrylic acid and alkyl methacrylate; copolymers of methacrylic acid, alkyl acrylate and alkyl methacrylate; copolymers of dialkylaminoethyl methacrylate, butyl methacrylate and methyl methacrylate; polyvinylacetal dialkylaminoacetate; and copolymers of (A) vinylpyridine or alkylvinylpyridine, (B) methacrylic acid and (C) alkyl acrylate.

4. The method according to claim 2 or 3, where the alkyl group contained in the coating polymer material has 1 to 4 carbon atoms.

5. The method according to claim 1, wherein said coating polymer material is selected from carboxymethyl ethylcellulose, cellulose acetate phthalate, hydroxypropyl methylcellulose phthalate, polyvinylacetal diethylaminoacetate, copolymers of dimethylaminoethyl methacrylate, methyl methacrylate and butyl methacrylate; copolymers of methacrylic acid, methyl acrylate and methyl methacrylate; copolymers of methacrylic acid and methyl methacrylate; copolymers of methacrylic acid and ethyl acrylate; copolymers of 2-vinylpyridine, methacrylic acid and methyl acrylate; and copolymers of 2-methyl-5-vinylpyridine, methyl acrylate and methacrylic acid.

6. The method according to claim 1, wherein said coating polymer material is present in an amount of about 0.02 to about 10 grams per gram of the pharmaceutically active compound.

7. The method according to claim 1, 2 or 3, wherein said pharmaceutically active compound has a particle size of about 5 to about 100μ, and said ethylcellulose has a viscosity of about 3 to about 500 cP when measured at 25° C. with respect to a 5 w/w % solution of said ethylcellulose in toluene-ethanol.

8. The method according to claim 1, 2 or 3, wherein said solvent is an alkanol having 1 to 4 carbon atoms, an alkanone having 3 to 5 carbon atoms, a mixture of said alkanol and said alkanone, or ethyl acetate.

9. The method according to claim 1, 2, or 3 further comprising adding a plasticizer to said solution.

10. The method according to claim 9, wherein said plasticizer is selected from the class consisting of glycerin monoacetate, glycerin diacetate, glycerin triacetate, propyleneglycol, polyvinylacetate, an ester of glycerin or acetylglycerin with an alkanoic acid having 10 to 18 carbon atoms; polyethyleneglycol, dialkylpolysiloxane, and polylactic acid, and is added in an amount of 0.01 to 1.0 gram per gram of said coating polymer material.

* * * * *